United States Patent [19]
Wurtman et al.

[11] Patent Number: 4,999,382
[45] Date of Patent: Mar. 12, 1991

[54] COMPOSITIONS FOR TREATING TOBACCO WITHDRAWAL SYMPTOMS AND METHODS FOR THEIR USE

[75] Inventors: Richard J. Wurtman; Judith J. Wurtman, both of Boston, Mass.; Bonnie Spring, Chicago, Ill.

[73] Assignee: Massachusetts Institute of Technology, Cambridge, Mass.

[21] Appl. No.: 262,625

[22] Filed: Oct. 26, 1988

[51] Int. Cl.$^5$ ............................................. A61K 31/135
[52] U.S. Cl. ..................................... 514/646; 514/813
[58] Field of Search .................................. 514/646, 813

[56] References Cited

FOREIGN PATENT DOCUMENTS

EP0153083 8/1985 European Pat. Off. .
WO88/03801 6/1988 PCT Int'l Appl. .

OTHER PUBLICATIONS

M. E. Benwell et al., *Journal of Neurochemistry*, 50(4): 1243-1247 (1988).
D. K. Hatsukami et al., *Psychopharmacology*, 84: 231-236 (1984).
N. G. Schneider and M. E. Jarvik, *Psychopharmacology*, 82: 143-144 (1984).
N. E. Grunberg, *Addictive Behaviors*, 7(4): 317-331 (1982).
N. E. Grunberg et al., *Psychopharmacology*, 87: 198-203 (1985).
E. Wong, *Can. Med. Assoc, J.*, 107: 727 (1972).
M. A. Jacobs et al., *Psychosom. Med.*, 33: 545-556.
B. Luban-Plozza, *Munch. Med. Wochenschr.*, 112: 2322-2327 (1970).
N. B. Edwards et al., *Psychosomatics*, 29: 203-206 (1988).
E. M. Sellers et al., *J. Clin. Psychopharmacol.*, 7: 417-420 (1987).
G. L. S. Pawan et al., *Br. J. Pharmacol.*, 41: 416P-417P (1971).
P. Turner et al., *Int. J. Obesity*, 6: 411-415 (1982).
Chem. Abst. 107-126038b (1987).

*Primary Examiner*—Stanley J. Friedman
*Attorney, Agent, or Firm*—Hamilton, Brook, Smith & Reynolds

[57] ABSTRACT

Compositions useful in the treatment of disturbances of appetite, disturbances of mood, or both, nicotine withdrawal associated as well as experienced by individuals after discontinuing tobacco use as methods of use therefor. The compositions include serotoninergic drugs, such as d-fenfluramine and fluoxetine.

3 Claims, No Drawings

COMPOSITIONS FOR TREATING TOBACCO WITHDRAWAL SYMPTOMS AND METHODS FOR THEIR USE

BACKGROUND

Discontinuing the use of nicotine is extremely difficult for many smokers; approximately 70% of those who seek help in formal treatment programs are no longer abstinent twelve months later. Jaffe, J. (1980) In: *The Pharmacological Basis of Therapeutics,* p. 535-584, A. G. Gilman, L. Goodman and A. Gilman eds., MacMillan Col, N.Y. Nicotine withdrawal causes symptoms that are most intense 48-72 hours after smoking is discontinued; they include increased anxiety, hostility and depression, as well as reduction in subjective vigor and impairment in concentration. D. K. Hatsukami et al. (1984) *Psychopharmacology,* 84:231-236. Subsequently, the withdrawn smoker experiences the absence of nicotine's reinforcing properties: muscle relaxation, reduction of irritability, facilitation of alertness, and suppression of appetite.

The ex-smoker is also at risk for weight gain, the most reliably demonstrated behavioral consequence of smoking cessation. J. D. Matarazzo (1984) In: *Psychology and Health,* Vol. 3, p. 7-43, B. L. Hammonds and C. J. Scheirer (Eds.) Amer. Psych. Ass'n, Washington, D.C. In a majority of rats and humans, the weight gain is generated primarily by increased consumption of high-carbohydrate foods. N. E. Grunberg, 1982, *Addictive Behaviors,* 7:317-331; N.E. Grunberg et al., 1984, *Psychopharmacology,* 83:93-98; N. E. Grunberg et al., 1985, Psychopharmacology, 87:198-203.

Because of the adverse effects of smoking on health and the difficulty so many smokers encounter in giving up smoking, it would be very useful to have an effective smoking cessation method.

SUMMARY OF THE INVENTION

The present invention is based on the discovery that administration of an agent which selectively enhances serotonin-mediated neurotransmission is useful in suppressing the weight gain and recidivism that usually follows attempts to give up smoking. The present invention relates to compositions which include one or more of such agents and to methods of reducing or preventing the weight gain and recidivism which usually accompany or follow attempts to stop smoking. Agents or drugs useful in enhancing serotonin-mediated neurotransmission, or the effect of serotonin within the brain synapses, are referred to as serotoninergic drugs and include (1) drugs which act to increase the quantity of serotonin present within the synapses and (2) drugs which activate post-synaptic serotonin receptors.

Drugs which act to increase the quantity of serotonin within brain synapses include those which act to increase serotonin production, cause or facilitate its release, or suppress its reuptake; those which block presynaptic receptors; and those which block the activity of monoamine oxidase. Related drugs, the serotonin agonists, share with these drugs the ability to enhance serotonin-mediated neurotransmission.

One or more of these serotoninergic drugs can be administered to an individual in an amount effective to reduce or prevent the effects, such as appetite and mood disturbances associated with nicotine withdrawal, as well as the weight gain and recidivism which frequently follow attempts to give up smoking.

In one embodiment of the present invention, d-fenfluramine, d,l-fenfluramine, d-norfenfluramine or d,l-norfenfluramine, which act to release serotonin and inhibit its inactivation by reuptake, is administered to individuals, who are attempting to quit smoking in a quantity sufficient to ameliorate or prevent the mood disturbances and/or to suppress the weight gain frequently evident in individuals trying to give up smoking, as well as to reduce recidivism. In a further embodiment, fluoxetine, which acts to inhibit reuptake of serotonin, is administered in a quantity sufficient to the same beneficial effects.

Administration of a serotoninergic drug according to the method of the present invention is of great benefit to persons who experience disturbances of mood and/or appetite associated with giving up smoking, because the drug or drugs administered act to alleviate or prevent such adverse symptoms.

DETAILED DESCRIPTION OF THE INVENTION

The present invention relates to compositions useful in alleviating or preventing disturbances of mood and/or appetite which occur when an individual stops using tobacco, as well as to methods of their use in treating such disturbances. Such compositions include one or more serotoninergic agents or drugs (i.e., one or more agents or drugs which selectively enhance serotonin-mediated neurotransmission).

Serotoninergic drugs included in compositions of the present invention act to enhance serotonin-mediated neurotransmission by increasing the quantity of serotonin present within brain synapses, by activating post-synaptic serotonin receptors, or both. One or more of such serotoninergic drugs may be present in a composition of the present invention and may be present alone (i.e., only serotoninergic drug(s)) or in combination with other substances which function in another capacity (e.g., as a filler, binder, etc.), as described below.

The neurotransmitter serotonin (5-hydroxytryptamine or 5-HT) is 3-(beta-aminoethyl)-5-hydroxyindole. It stimulates or inhibits a variety of smooth muscles and nerves and, among others, has effects on secretion by both exocrine and endocrine glands and on functioning of the respiratory, cardiovascular and central nervous systems. Within the central nervous system (CNS), serotonin serves as a neurotransmitter in the brain and spinal cord, where it is the chemical transmitter of neurons referred to as tryptaminergic or serotoninergic neurons. These neurons are involved in control of sleep, appetite, nutrient selection, blood pressure, mood, endocrine secretion, aggressivity and numerous other sensitivities to external stimuli. Without wishing to be bound by theory, it is believed that smoking may increase the number of receptors for nicotine on serotonin-releasing neurons. Therefore, in the absence of nicotine, serotoninergic neurons are firing less frequently, thereby releasing less serotonin. Thus, giving a serotoninergic drug that releases serotonin and/or blocks its reuptake benefits those trying to give up smoking or otherwise using (e.g., chewing) tobacco.

Numerous substances or drugs have been shown to affect serotonin activity. For example, endogenous serotonin levels can be increased by administering tryptophan, the precursor of serotonin. Fernstrom, J. D. and Wurtman, R. J., *Science,* 173:149-152 (1971).

It has now been discovered that administration of an agent or a drug which selectively enhances serotonin-mediated neurotransmission suppresses the weight gain and the increased appetite, particularly for carbohydrates (which results in overeating), as well as decreasing the depression and other negative mood states (e.g., depression, lethargy, anxiety, subjective tiredness, loss of energy, crankiness), which many smokers experience upon giving up tobacco and which may contribute to recidivism. An agent or a drug which selectively enhances serotonin mediated neurotransmission has been shown to be particularly effective in having these effects.

Although the basis for the discovered effect on individuals attempting to stop using tobacco is not known, there is a good theoretical basis for the effects. For example, as described by Benwell et al., the number of receptors for nicotine (and, thus, for acetyl choline) which can react with "nicotine" and "muscarinic" receptors was increased in post mortem brain samples from smokers (explicitly those on serotonin-releasing neurons—those of the median raphe nuclei). This implies that, in the absence of nicotine, the serotoninergic neurons are firing less frequently and, thus, releasing less serotonin. Therefore, administering a drug that enhances serotonin release and/or blocks its inactivation will be helpful.

Benwell et al. reported in the *J. Neurochem,* 50(4):1243-1247 (1988) that in a postmortem study of nicotinic receptors in the human brain, cigarette smoking was found to be associated with increased binding of (−)-[3H]nicotine binding to membranes prepared from the gyrus rectus, hippocampal neocortex, cerebellar cortex, hippocampal formation (Ammon's horn+subiculum), and the median raphe nuclei of the midbrain. Analysis of the binding data suggested that the increased binding reflected an increase in the density of the receptors, rather than a change in their affinity for (−)-nicotine. Benwell and co-workers report that the effects of smoking were not influenced significantly by either the sex or age of the subject. It was concluded that smoking evoked an increase in high-affinity nicotine binding similar to that observed previously in animals treated chronically with nicotine and that the effect of smoking on these sites is probably caused by the nicotine present in the tobacco smoke.

Administration of a drug (or drugs) which enhances serotonin-mediated neurotransmission by increasing the quantity of serotonin within brain synapses or by activating post-synaptic serotonin receptors results in amelioration or elimination of these commonly-experienced adverse effects.

For example, it has been shown that administration of d-fenfluramine (an anorectic drug) to ex-smokers results in a decreased weight gain and in lowered consumption of high-carbohydrate foods than observed when the subjects were not given the drug (i.e., were given a placebo). A d-fenfluramine racemic mixture, d,l-fenfluramine, would have the same effect, as would fenfluramine's principal metabolite, norfenfluramine.

Similarly, administration of fluoxetine, which suppresses reuptake of serotonin and, thus, increases the quantity of serotonin available at brain synapses, has been shown to result in weight loss in an individual who, while attempting to stop smoking without benefit of fluoxetine, had gained weight. One subject being treated with fluoxetine reported that cigarettes did not taste as "attractive as they used to" (i.e., prior to treatment with the drug), and that the drug enabled her to reduce smoking.

In place of, or in addition to, d-fenfluramine, d,l-fenfluramine and fluoxetine, other drugs which have the effect of enhancing serotonin-mediated neurotransmission can be administered. For example, the quantity of serotonin present at a given time or over a period of time can be enhanced by administering a drug which has any of the following effects:

1. increases serotonin production (e.g., tryptophan, lithium);
2. causes serotonin release, e.g., d-fenfluramine, d,l-fenfluramine, d-norfenfluramine or d,l-norfenfluramine;
3. suppresses serotonin reuptake, e.g., fluoxetine, fluvoxamine, citalopram, chlorimipramine (also known as clomipramine) femoxetine, cianopramine, ORG 6582, RU 25591, LM5008, sertraline or 1S-4S-N-methyl-4-(3,4 dichlorophenyl)-1,2,3,4,-tetrahydro-1-naphthylamine, paroxetine, DU 24565, indalpine, CGP 6085/A, WY 25093, alaprociate, zimelidine, cyanimipramine, desyrel (trazodone hydrochloride) or trazodone amitriptyline or elavil (amitriptyline hydrochloride), imipramine or tofranil (imipramine hydrochloride), trimipramine or surmontil, doxepin or sinequan (doxepin hydrochloride), protriptyline or vivactil (protriptyline hydrochloride), nortriptyline or aventyl (nortriptyline hydrochloride), dibenzoxazepine (also known as amoxapine or asendin);
4. blocks presynaptic receptors, e.g., metergoline, methysergide, cyproheptadine (which can also block postsynaptic receptors); or
5. blocks monoamine oxidase, e.g., deprenyl, marplan or isocarboazide, nardil (phenelzine sulfate) or phenelzine, parnate (tranylcypromine sulfate) or tranylcypromine, furazolidone, procarbazine, moclobemide or aurorix, brofaromine).

The chemical names of DU 24565, CGP 6085/A, and WY 25093 are, respectively, 6-nitroquipazine, 4-(5,6-dimethyl-2-benzofuranyl) piperidine HCl, and 1-[1-([indol-3-yl]methyl) piperid-4-yl]-3-benzoylurea, respectively. Classen, K., et al., *Naunyn Schmiedebergs Arch. Pharmacol.,* 326(3): 198-202 (1984); Kulakowski, E. C. et al., *Clin. Exp. Hypertens.* [A], 7(4): 585-604 (1985); Diggory, G. L. et al., *Arch. Int. Pharacodyn. Ther.,* 248(1): 86-104 (1980).

Alternatively, serotonin-mediated neurotransmission can be enhanced by administering a drug, such as quipazine, m-CPP, MK212 or CM57493, which activates post-synaptic serotonin receptors.

In either case, such agents or drugs can be administered individually or in combination. The quantity of an individual drug to be administered will be determined on an individual basis and will be based at least in part on consideration of the individual's size, the severity of symptoms to be treated and the result sought.

The agent(s) or drug(s) can be administered orally, by subcutaneous or other injection, intravenously, parenterally, transdermally, or rectally. The form in which the drug will be administered (e.g., powder, tablet, capsule, solution, emulsion) will depend on the route by which it is administered.

The composition of the present invention can optionally include, in addition to the serotoninergic drug or drugs, other components. The components included in a particular composition are determined primarily by the manner in which the composition is to be administered. For example, a composition to be administered orally in tablet form can include, in addition to one or more serotoninergic drugs, a filler (e.g., lactose), a binder (e.g., carboxymethyl-cellulose, gum arabic, gelatin), an adjuvant, a flavoring agent, a coloring agent and a coating material (e.g., wax or a plasticizer). A composition to be administered orally, but in liquid form, can include one or more serotoninergic drugs, and, optionally, an emulsifying agent, a flavoring agent and/or a coloring agent.

In general, the composition of the present invention is administered to an individual prior to or after the individual discontinues tobacco use. The length of time during which the drug (or drugs) is administered varies on an individual basis and can continue until the desired result is achieved (i.e., reduction in or cessation of tobacco use). In general, the drug or drugs will be administered for a period of from about 1 to about 3 months, although repeated periods of treatment may be necessary. The dose of serotoninergic drug administered daily will also vary on an individual basis and to some extent will be determined by the type and severity of symptoms to be treated. If the serotoninergic drug administered is d-fenfluramine a dose of from approximately 15 mg/day to approximately 45 mg/day is administered. For d,l-fenfluramine, a dose of approximately 30 mg/day to approximately 120 mg/day is administered. As described in Example I, 30 mg/day of d-fenfluramine, given in two doses, has been shown to be effective in suppressing weight gain in subjects. In the case of fluoxetine administration, a dose of from approximately 20 mg/day to approximately 120 mg/day is administered. As described in Example II, a dose of 40 mg/day of fluoxetine, (20 mg given twice daily) has been shown to be effective in ameliorating the weight gain and tobacco craving that the subject reported when on a placebo. The serotoninergic drug can be administered in a single dose or in a number of smaller doses over a period of time; for example, the 30 mg/day dose of d-fenfluramine can be administered in a series of smaller doses over the course of the day.

The present invention will now be illustrated by the following examples, which are not to be taken as limiting in any way.

EXAMPLE I

Assessment of effect of d-fenfluramine on weight gain recidivism associated with nicotine withdrawal Twenty-six subjects were recruited from the general community by newspaper advertisements, public service announcements, and medical education program newsletters as well as through personal and physical referral. They were offered a free smoking cessation treatment program if they agree to participate in the study.

Study candidates were screened by a personal interview and physical examination by a CRC nurse-practitioner that included a urinalysis, a CBC, and blood measurements including creatinine, cholesterol, total protein, triglycerides, bilirubin, alkaline phosphatase, DH, SGOT, sodium, potassium, chloride and $CO_2$. Persons 40 years or older also received an EKG. Subjects were not permitted to enter the study if they were pregnant or suffered from hypoglycemia, diabetes, anorexia, bulimia, hypertension, or had medically or self-imposed food restrictions. Subjects taking medications chronically were also not included in the study.

Individuals who met the eligibility criteria and who agreed to follow a smoking withdrawal treatment program were admitted to the study. They were randomly assigned on a double-blind basis to receive either drug or placebo. Twenty-six subjects entered the study in two groups of 13, one of which was given d-fenfluramine, the other was given placebo.

Subjects underwent two baseline measurements of their behavioral status and weight prior to their withdrawal from smoking. The first pre-drug, pre-withdrawal baseline was taken 6–9 days prior to smoking cessation (Days 1, 2, and 3 before drug treatment began). The second on-drug, prewithdrawal baseline was taken for several days prior to terminating smoking (Days −2 to 0) after subjects have been started on drug or placebo. Assessments were repeated during the first week of nicotine withdrawal and then occurred weekly through the first four weeks of smoking cessation.

Participants filled out questionnaires about mood and withdrawal symptoms for a series of intervals (up to three days) before smoking cessation, during the initial week of nicotine withdrawal (Days 1–7), and during the next three weeks of smoking cessation (Days 12–14, 19–21, 27–29). Cognitive performance was tested in the laboratory twice before smoking withdrawal (Days p 3 and 0), and during the first (Day 2) and fourth (Day 29) weeks of smoking cessation. Food intake was also measured over a 48 hour period 2–3 days before smoking cessation, and days 1–2, and days 28–29 after smoking cessation.

The smoking withdrawal treatment program followed a format worked out by professional groups dedicated to smoking cessation. The first group behavioral treatment session took place one week prior to terminating smoking. After this session subjects began taking drug or placebo. The second group session occurred one week later, at which time the participants stopped smoking. The group met again after two days, one week, and four weeks of smoking cessation.

Drug Treatment

Subjects received d-fenfluramine (two 15 mg doses; one taken upon arising and the second 12 hours later), or placebo (administered in the same schedule). To ensure that drug levels were constant prior to the first nicotine withdrawal assessment period, all subjects received drug or placebo for 6–7 days before they stopped smoking.

Behavioral Treatment

Behavioral treatment, administered by an experienced group facilitator, involved traditional smoking cessation techniques. These included: (1) information about the short- and long-term consequences of smoking; (2) information about the cessation process; (3) identification of triggers and reinforcements for smoking; (4) identification and implementation of substitute responses, counter-motivations, and self-management strategies; (4) rapid smoking; (5) telephone support network; and (6) relapse prevention.

Measurement of Smoking Abstinence

To monitor adherence to the smoking withdrawal program, subjects were asked to provide self-reports of any cigarettes smoked in the time preceding their attendance at the group treatment sessions. In addition, a noninvasive ecolyzer measurement of exhalation levels of carbon monoxide is taken each time the subject returned to the CRC for assessment, treatment, or medication. In this test, the subject inhaled deeply and then exhaled so as to blow up a balloon via a glass tube. When the tube was placed over its sensor, the ecoloyzer, a small recording box, yielded a measure of expired carbon monoxide. A value of 8 parts per million or greater suggests nonabstinence.

Behavioral Assessments

Subjects filled out questionnaires about withdrawal symptoms and mood on each of the three days prior to smoking cessation, and days 7, 12 to 14, 19 to 21, and 27 to 29 after smoking cessation. They completed the questionnaires between 6:00–7:00 p.m., prior to eating supper. Tests of cognitive performance were administered on Days p 3, 0, 2, and 29 when the subject visits the CRC. Five subjects underwent simultaneous computerized cognitive testing between 6:00–6:30 p.m. The remaining five subjects completed mood and withdrawal questionnaires until they underwent computerized testing between 6:30–7:00 p.m. On evenings when a smoking cessation group treatment session is scheduled, subjects ate a boxed supper between 7:00–7:30 p.m.; they participated in a smoking cessation group treatment session between 7:30–9:00 p.m.

Measurement of Food Intake

Food intake was assessed at three periods: 2–3 prior to medication and smoking cessation, days 1–2 of nicotine withdrawal, and days 28–29 after smoking withdrawal. Each assessment period measured food consumed at 6 meals over two days and snacks consumed between and after meals during the same period. Subjects were offered two carbohydrate-rich and two protein-rich foods at every meal. The foods were provided in pre-weighed containers and subjects had unlimited access to these foods. All the foods contained approximately 120 calories per serving and were low in fat. In addition, subjects were given containers with 4 high carbohydrate snack choices. Two of the snacks were starchy, crunchy carbohydrates (oyster and goldfish crackers) and two were chewy, sweet carbohydrate (jelly beans and gumdrops). All snacks were packaged in pre-weighed containers and contain about 110 calories per serving. All snacks were low fat. Each snack package contained a colored label that the subject will remove when the snack was consumed. The food record was set up so that the subject could indicate the time of day when the snack was consumed. The snacks were given to the subject following each meal on day 1 of food intake measurement and the snack food records returned with the uneaten snacks at the following meal. On day two, subjects turned in their snack food records at the end of the evening smoking group treatment session.

During the food intake measurement period, subjects were asked to refrain from eating foods not supplied by the CRC and to refrain from consuming sugar-sweetened beverages.

Subjects were given diet counseling, if requested, at the end of the smoking cessation program. They were told that such counseling will be based, in part, on their food intake patterns obtained during these measurement periods. Subjects were given any instructions concerning their food intake during the rest of the study except to refrain from following any formal weight loss program.

Results

Weight changes of the twenty-six participants were measured for 29 days (off cigarettes), and it was determined whether or not they were able to remain off cigarettes. The subjects receiving placebo gained, on average, 3.42 pounds; those receiving d-fenfluramine lost, on average, 1.77 pounds. Sixty-two percent of those on d-fenfluramine were able to remain off cigarettes during the 29-day test period; only thirty-nine percent of the placebo group succeeded in doing so.

EXAMPLE II

Assessment of the effect of fluoxetine on weight gain and recidivism associated with nicotine-withdrawal A small-scale study was performed to assess the effects of fluoxetine. One of the subjects who had been in the placebo group of the above study in Example I was given fluoxetine (20 mg twice daily) for twelve days (in an open-label study) following the protocol set out in Example I. The individual—who had gained weight (5 lbs.) during the prior placebo period—lost two pounds during the 12-day test period, and cut her daily cigarette consumption down from 12–13 to 1–2. She noted that her appetite was "reduced to normal" and "cigarettes don't taste as attractive as they used to".

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A method of treating disturbances of mood, disturbances of appetite or disturbances which contribute to recidivism associated with nicotine withdrawal comprising administering to a human experiencing symptoms of nicotine withdrawal an effective quantity of a drug which selectively enhances serotonin-mediated neurotransmission selected from the group consisting of d-fenfluramine, d,l-fenfluramine, d-norfenfluramine, d,l-norfenfluramine and fluoxetine.

2. A method of ameliorating disturbances of mood, disturbances of appetite or disturbances which contribute to recidivism associated with nicotine withdrawal comprising administering to a human prior to or after discontinuing tobacco use a composition comprising an effective quantity of a serotoninergic drug selected from the group consisting of: d-fenfluramine, d,l-fenfluramine, d-norfenfluramine, d,l-norfenfluramine and fluoxetine.

3. A method of preventing a return to tobacco use by a human who has stopped using tobacco comprising administering to said human an effective quantity of a drug which selectively enhances serotonin-mediated neurotransmission selected from the group consisting of: d-fenfluramine, d,l-fenfluramine, d-norfenfluramine, d,l-norfenfluramine and fluoxetine.

* * * * *

UNITED STATES PATENT AND TRADEMARK OFFICE
CERTIFICATE OF CORRECTION

PATENT NO. : 4,999,382
DATED : March 12, 1991
INVENTOR(S) : Richard J. Wurtman, Judith J. Wurtman, Bonnie Spring It is certified that error appears in the above-identified patent and that said Letters Patent is hereby corrected as shown below:

The first paragraph of the text of the patent should read:

-- Government Support

This invention was made with government support under Grant Number NIH05-M01-RR00088 awarded by the National Institutes of Health. The government has certain rights in the invention. --

Signed and Sealed this

Twenty-ninth Day of May, 2001

*Attest:*

NICHOLAS P. GODICI

*Attesting Officer*  *Acting Director of the United States Patent and Trademark Office*